United States Patent [19]

Gay

[11] Patent Number: 4,615,468

[45] Date of Patent: Oct. 7, 1986

[54] GAS AMPOULE-SYRINGE

[75] Inventor: Don D. Gay, Aiken, S.C.

[73] Assignee: The United States of America as represented by the United States Department of Energy, Washington, D.C.

[21] Appl. No.: 704,455

[22] Filed: Feb. 22, 1985

[51] Int. Cl.$^4$ .............................. F17B 1/14; F17B 1/10
[52] U.S. Cl. .................................... 222/327; 206/0.6; 220/429; 220/256; 220/288; 604/235; 422/102; 422/100; 73/864.91
[58] Field of Search ........... 73/864.91, 864.81, 864.82, 73/864.83, 864.84, 864.85, 864.86, 864.87; 422/100, 102; 222/387, 386, 3, 5, 327, 82, 89, 131; 141/19, 27; 220/429, 256, 288; 206/0.6, 0.7, 528, 530, 531, 532; 604/232–235

[56] References Cited

U.S. PATENT DOCUMENTS

| 361,891 | 4/1887 | Phelan | 222/386 X |
|---|---|---|---|
| 1,673,599 | 6/1928 | Smith | 220/256 |
| 2,236,727 | 4/1941 | Dewees | 222/386 |
| 2,354,649 | 8/1944 | Bruckner | 222/386 X |
| 2,593,552 | 4/1952 | Folkman | 222/5 |
| 2,650,591 | 9/1953 | Love | 222/327 X |
| 3,141,583 | 7/1964 | Mapel et al. | 222/327 X |
| 4,133,736 | 1/1979 | Nakagawa et al. | 73/864.74 X |
| 4,377,949 | 3/1983 | Tucker et al. | 73/863.83 X |

FOREIGN PATENT DOCUMENTS 806429 12/1936 France .............................. 604/232

OTHER PUBLICATIONS

"A Calibrated Dose Dispenser for Gaseous $^{133}$Xe"; *J. Nucl. Med. (USA)*; Dec. 1975; vol. 16, No. 12, pp. 1197–1199; Robert F. Gutkowski et al.

*Primary Examiner*—Stewart J. Levy
*Assistant Examiner*—Tom Noland
*Attorney, Agent, or Firm*—Allen F. Westerdahl; Judson R. Hightower

[57] ABSTRACT

A gas ampoule for the shipment and delivery of radioactive gases. The gas ampoule having a glass tube with serum bottle stopper on one end and a plunger tip in the opposite end all fitting in a larger plastic tube threaded on each end with absorbent between the tubes, is seated onto the internal needle assembly via a bushing associated with the plunger and locked into the syringe barrel via barrel-bushing locking caps. The design practically eliminates the possibility of personnel contamination due to an inadvertent exposure of such personnel to the contained radioactive gas.

16 Claims, 5 Drawing Figures

GAS AMPOULE-SYRINGE

CONTRACT STATEMENT

The United States Government has rights in this invention pursuant to Contract No. DE-AC09-76SR00001 between the U.S. Department of Energy and E. I. DuPont de Nemours & Co.

BACKGROUND OF THE INVENTION

1. Field of the Invention

The invention relates to a disposable gas ampoule for containing a gas and to a syringe for using such ampoule.

2. Discussion of Background and Prior Art

U.S. Pat. No. 4,377,949 discloses a mobile sampler for use in acquiring samples of terrestrial atmospheric gases from a free body of such gases. The device has a plurality of tubular bodies adapted to be mounted in side-by-side relation on a motorized highway vehicle in mutual parallelism with the axis of the normal path of travel for the vehicle. Each of the bodies has a cylindrical configuration and has an axial opening disposed at each of its opposite ends, whereby a linear flow path is defined therethrough. A pair of pivotally-supported, spring-biased sealing caps are mounted adjacent to the ends of the body and are continuously urged into hermetic sealing relationship therewith. There is a restraint for securing the caps against spring-urged pivotal displacement. There is an operable release mechanism for simultaneously releasing the caps for spring-urged displacement. The mechanism includes a hot wire cutter for separating the line. Thereby samples of air are trapped in the body as the caps are spring-driven to assume a hermetically-sealed relation with the openings defined in each of the opposite ends of the body.

SUMMARY OF THE INVENTION

An object of the invention is to provide a disposable gas ampoule for holding a gas, such as, a radioactive gas. Another object of the invention is to provide a syringe adapted to use such disposable gas ampoule. Other objects and advantages of the invention are set out herein or are obvious herefrom to one ordinarily skilled in the art.

The objects and advantages of the invention are achieved by the disposable gas ampoule and syringe therefor of the invention.

To achieve the foregoing and other objects and in accordance with the purpose of the invention, as embodied and broadly described herein, the invention involves a disposable gas ampoule holding or containing a gas, such as, a radioactive gas. The disposable gas ampoule includes a cylindrical glass tube, which is adapted to hold the gas, and a layer of absorbent material, which circumscribes and contacts the cylindrical glass tube and which adsorbs any of the gas which may have passed through the cylindrical glass tube. There is a plastic tube which circumscribes and contacts the absorbent material layer and which is externally threaded on each end portion. A cap is threaded onto the first end of the plastic tube. There is also a cylindrical block which is positioned in the first end of the cylindrical glass tube adjacent to the plastic cap, which contacts the cylindrical glass tube, which is composed of a framed material and which is impregnated with a gas absorbent material. A cylindrical plunger tip is located in the cylindrical first end of the glass tube in the cylindrical block. There is an end stopper which has a central shaft that is positioned in the second end of the cylindrical glass tube. The central cylindrical shaft contacts the cylindrical glass tube. The end stopper has an outer rim that extends outward beyond the second end of the cylindrical glass tube and has an outer lip that is affixed to the outer rim thereof, that contacts the outside of the second end of the cylindrical glass tube and that is positioned within the plastic tube. A cap is threaded onto the second end of the plastic tube.

The cylindrical glass tube is preferably made from glass tubing that has an internal diameter ±0.0004 inch, consistently, such as "Trubore Tubing" of Ace Glas Co. The absorbent material layer is preferably composed of activated charcoal. Preferably the plastic tube is composed of relatively shatter-proof plastic. Also preferably the two caps are composed of relatively shatter-proof plastic or of metal, and preferably the cylindrical block is composed of plastic or teflon. The gas absorbent material impregnated in the cylindrical block is preferably composed of activated charcoal. Preferably the plunger tip is composed of teflon, and preferably the stopper end is composed of teflon.

The invention also includes a combination of the disposable gas ampoule of the invention and a syringe adapted to operably interface with the gas ampoule. The syringe has a cylindrical barrel. The disposable gas ampoule is positioned within the cylindrical barrel of the syringe. The caps are removed from the ends of the gas ampoule. The cylindrical block is also removed from within the cylindrical glass tube. The syringe also has a bottom plate located on its second end. A hollow syringe needle is positioned through the central axis of the bottom plate and is perpendicular to the bottom plate. The other end of the needle located within the syringe barrel has been forced through the end stopper at its central axis. A mechanism for opening and closing the needle is positioned between the bottom plate of the syringe and the end stopper. The opening-and-closing mechanism is manually operable by at least one arm thereof which extends outward beyond the syringe barrel. The syringe further has a plastic bushing positioned in the first end of the cylindrical bushing. The plastic bushing has a longitudinal central bore. A plunger is positioned with its shaft slidably mounted in the longitudinal central bore of the plastic bushing and with its plunger end mounted in the cylindrical glass tube in a slidable manner between the cylindrical plunger tip and the first end of the glass tube. The syringe barrel has a rim at the end located near the plastic bushing. The plastic bushing has a rim on its outer end which overlaps and contacts the rim of the syringe barrel. A removable locking cap fits over the rim of the syringe barrel and the rim of the plastic bushing.

Preferably the plastic bushing is composed of plastic or teflon. The central bore of the plastic bushing contains holes filled with an absorbent. Also, preferably such absorbent is activated charcoal.

The gas-ampoule and syringe of the invention have been designed for use in procedures and experiments utilizing radioactive gases, but are not limited to such gases. The invention design is consistent with the unit-dose concept in which only the amount-concentration of material needed for one exposure is contained in the invention ampoule. Such makes the invention ampoule disposable and eliminates the long-term storage of a large amount of stock material at large concentrations for use over extended periods of time. The invention gas-ampoule locks into the invention syringe for injection of the gas into a desired exposure chamber, vessel or other container. The safety features built into the invention gas ampoule include a glass tube within a plastic tube with an absorbent powder filling the space between. Plastic end caps screw onto the outer plastic tube, making a gas-tight, almost leak-proof container. The syringe barrel holds the entire invention gas ampoule minus its end caps. The absorbent-impregnated foam block of the invention ampoule is also removed when the invention ampoule is inserted in the invention syringe. A gas permeable bushing associated with the syringe plunger seats the invention gas ampoule onto the needle assembly and, with barrel-bushing locking caps, its locks and ampoule and plunger in the barrel making accidental withdrawl impossible. The needle assembly has a Pressure-Lok ® type mechanism with open and closed positions preventing the accidental injection of the radioactive gas. Pressure-Lok ® is a registered trademark of Precision Sampling Corporation, P.O. Box 15119, Baton Rouge, La. 70895.

The advantages of the invention gas ampoulesyringe combination reside in the effective utilization of the unit-dose concept for storage and delivery of only that amount of radioactive gas actually needed for individual exposure or experimental purposes and the inherent safety features of the invention gas ampoule-syringe. The individual unit-dose gas ampoules can be packaged and shipped more safely with less chance of all of them breaking (if more than one is shipped per unit of time) than with one large, concentrated stock container. Also, the total amount of radioactive gas purchased for an experiment should be decreased because the invention product can bring about multiple shipments for use when the radioactive gas is actually needed, thereby eliminating the waste of not using all of the radioactive gas that is purchased. Such will significantly reduce the total amount of radioactive gas physically stored in a regulated area waiting to be used.

The safety features inherent in the invention product practically eliminate the chances for accidental releases and subsequent personnel exposures. The absorbent material surrounding the glass inner tube provides an absorption mechanism for any accidentally broken glass tubes, and along with the outer plastic tube, provides a cushion against breakage should a gas ampoule be dropped. The Pressure-Lok ® type open and closed mechanism associated with the needle and the plastic, gas permeable bushing associated with the plunger insure that once the gas ampoule is locked into the syringe barrel via the barrel-bushing locking caps, the radioactive gas cannot be released except by design.

Uses for the invention gas ampoule-syringe are with every investigator using radioactive gases for experimental purposes and with every lab technician using radioactive gases for routine procedures. Although the cost per unit of activity (dollars per millicurie, microcurie, nanocurie, etc.) would probably increase, the total cost is expected to be only slightly higher (if at all) because there will be no wasted material not used but requiring disposal. On a cost-benefit basis the invention product would be competitively affordable and would be preferred because the inherent safety features, the small amount of radioactivity contained in each gas ampoule, the less stringent storage requirements necessary for minute amounts of radioactivity and the relative ease of disposing of the empty ampoules versus the disposal of partially-filled, high activity stock containers.

The individual unit-dose and the gas ampoule-syringe should revolutionize the way in which nuclear material-producing companies offer radioactive gases as well as the manner in which personnel involved with the use of radioactive gases design and execute experiments and routine procedures.

Reference is now made in detail to the present preferred embodiment of the invention, an example of which is illustrated in the accompanying drawing.

A BRIEF DESCRIPTION OF THE DRAWING

The accompanying drawing, which is incorporated in and form a part of the specification, illustrates the invention and, together with the description, serves to explain the principles of the invention. In the drawing.

DETAILED DESCRIPTION OF THE INVENTION

All parts, percentages ratios and proportions are on a weight basis unless otherwise stated herein or obvious herefrom to one ordinarily skilled in the art.

Figure 1:
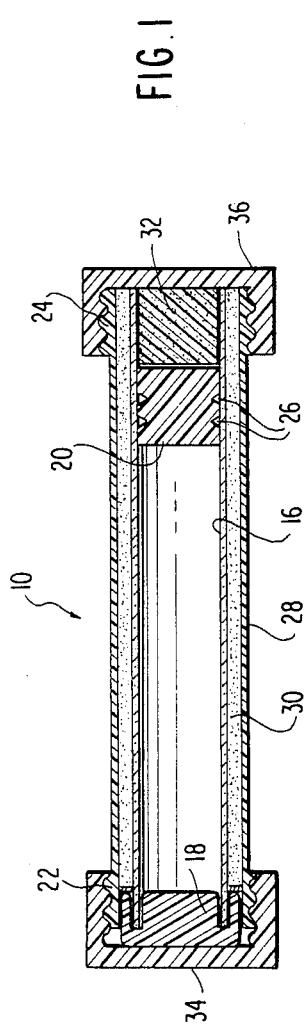
FIG. 1 is a cross-sectional longitudinal view of disposal gas ampoule of the invention.
Figure 2:
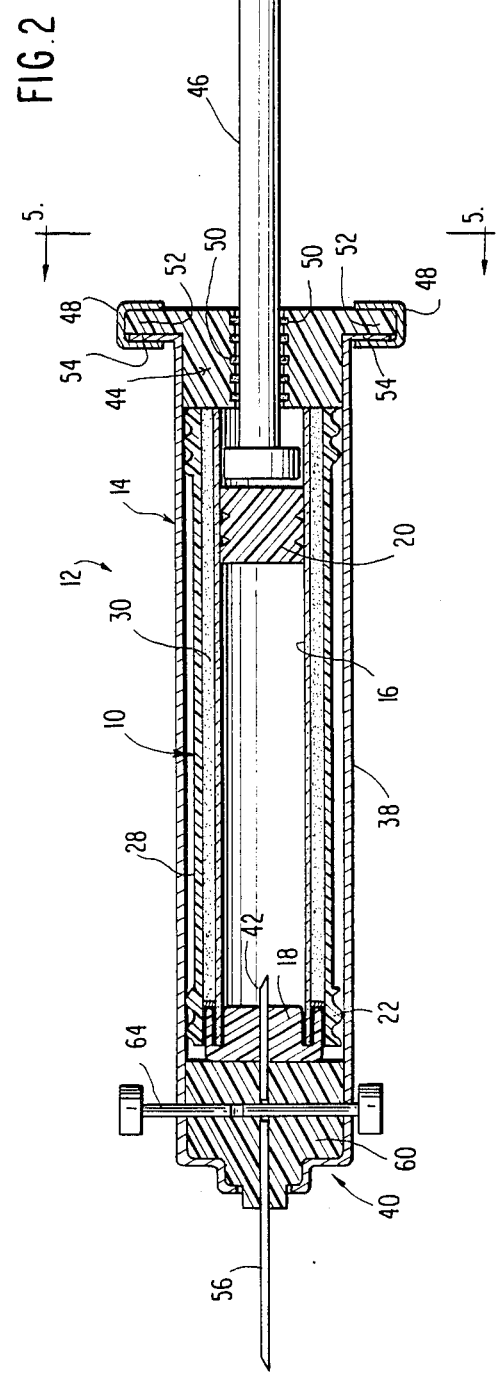
FIG. 2 is a partially-cutaway cross-sectional longitudinal view of the syringe-gas ampoule of the invention.

Referring to FIG. 1, a preferred embodiment is disclosed which shows disposable gas ampoule 10 of the invention. Referring to FIG. 2, a preferred embodiment which shows combination 12 of disposable gas ampoule 10 and syringe 14, which is adapted to operably interface with syringe 10. Disposable gas ampoule 10 provides a radioactive gas shipment container. Combination 12 of disposable gas ampoule 10 and syringe provides an apparatus for delivery of a radioactive gas.

Gas ampoule-syringe 12 has two discreet components, namely, gas ampoule 10 containing the radioactive gas and syringe 14 which delivers the radioactive gas. Gas ampoule 10 is disposable. Gas ampoule 10 includes glass tube 16 which has (teflon or teflon-coated) serum bottle-type stopper 18 glued on one end and (teflon or teflon-coated) gas-tight plunger-tip 20 inserted into the other end (see FIG. 1). Tube 28, externally threaded on each end (22, 24), fits over glass tube 16. Plastic tube 28 and glass tube 16 have a small gap between them. Several small blocks (not shown) are mounted in the gap between glass tube 16 and plastic tube 28 to maintain them in fixed relationship to each other. Plunger tip 20 preferably has two circumscriptional grooves 26. By using plunger tip 20 with a slightly larger diameter than the internal diameter of inner glass tube 16, plunger tip 20 fits in an air tight manner in inner glass tube 16 with grooves 26 providing expansion room for the extended surfaces of plunger tip 20. Plunger tip 20 is preferably composed of teflon. Plastic tube 28 has an inside diameter permitting it to fit snugly over serum bottle stopper 18. Serum stopper 18 is glued to the inside of plastic tube 28 to make it gas tight. The space between glass tube 16 and plastic tube 28 is filled with powdered absorbent 30. The open end between tubes 16 and 28 opposite the serum stopper 18 is sealed with epoxy or other material to contain activated charcoal and to make the assembly gas tight. Internal plunger tip 20 is positioned so that approximately 10 mm of space is left behind plunger tip 20.

Using a fine needle (not shown) inserted through serum stopper 18, glass tube 16 is partially evacuated and the desired amount for the unit dose of radioactive gas is introduced into glass tube 16 up to normal atmospheric pressure. After the needle is withdrawn from serum stopper 18, a drop of a sealant is placed on serum stopper 18 to make sure that the hole from the needle is sealed. Serum stopper 18 is preferably composed of teflon. Piece or block 32 of foam impregnated with the absorbent (i.e., activated carbon) is placed behind plunger tip 20 inside glass tube 16. Block 32 is preferably composed of plastic or teflon. End caps 34 and 36 are screwed onto threaded, outer, plastic tube 28. Foam block 32 is used to prevent plunger tip 20 from moving backward in glass tube 16. The impregnation of block 32 with the absorbent is done as a safety measure. If plunger tip 20 is faulty and does not give a gas-tight seal in glass tube 16, any radioactive gas that leaks out will be adsorbed onto the adsorbent on block 32, thereby preventing a possible contamination to an individual removing screw cap 36. With end caps 34 and 36 and foam block 32 securely in place, gas ampoule 10 is ready for final packaging and shipment.

Figure 4:
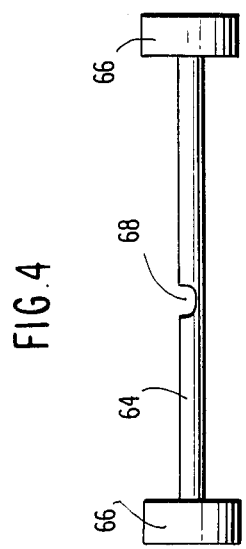
FIG. 4 is a top view of the closing-opening rod used in the invention syringe-gas ampoule.
Figure 5:
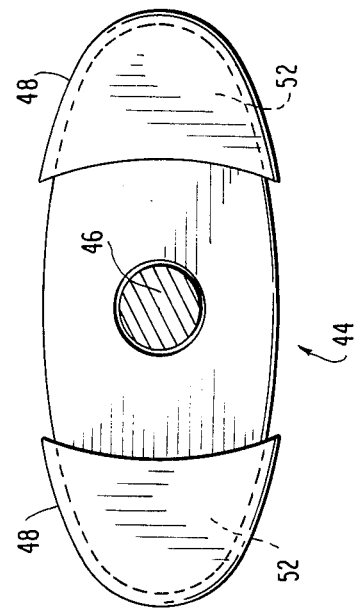
FIG. 5 is a top view along line 5—5 in FIG. 2.
Figure 3:
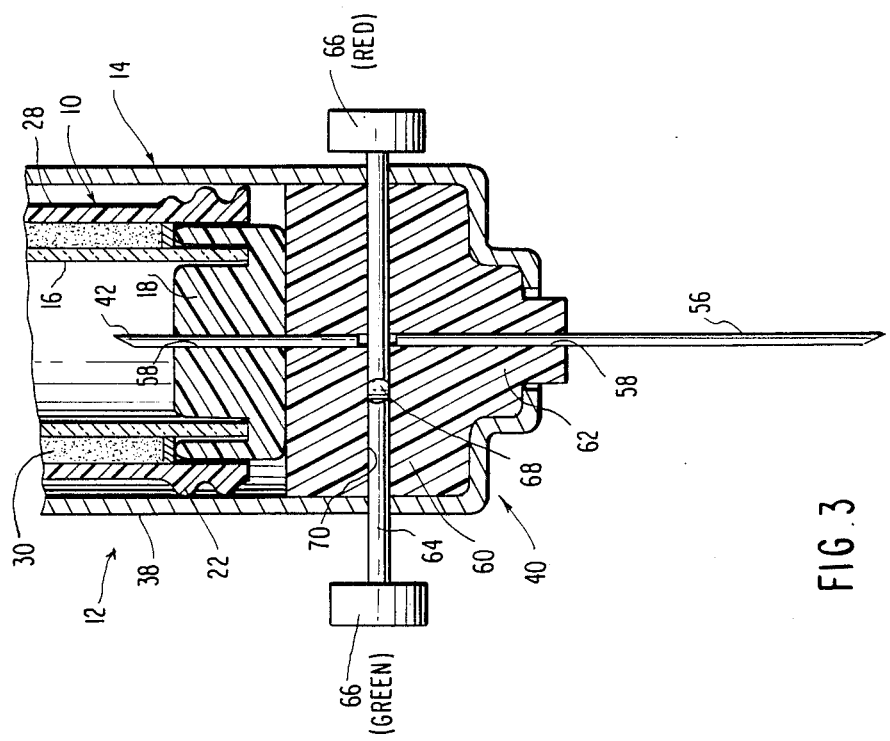
FIG. 3 is a partially-cutaway cross-sectional view of the needle end of the invention syringe-gas ampoule.

Referring to FIG. 2, syringe portion 14 of combined device 12 has an inside diameter (of syringe barrel 38) just large enough to accommodate the threaded plastic tube absorbent-glass tube assembly (collectively gas ampoule 10). Two additional safety features are incorporated into syringe 14. Pressure-Lok ® type mechanism 40 for needle 56 is used to open or close the flow path from ampoule 10 to and through needle 56. Such prohibits the release of any radioactive gas until lock mechanism 40 is manually switched to the open position. Cylindrical block 60 (preferably composed of teflon) is mounted in the bottom of syringe barrel 60. Block 60 contains bottom protrusion 62. Longitudinal passageway 58 is located on the longitudinal axis of the block. Lower needle segment 56 is mounted in the lower end of passageway 58, and upper needle segment 42 is mounted in the upper end of passageway 58. Upper needle segment 42 punctures and protrudes through stopper 18— see FIG. 2. Horizontal passageway 70 in block 60 intersects vertical passageway 58 as shown in FIG. 4. Rod 64 (preferably steel) slidably, but in a tight manner, fits in horizontal passageway 70. Vertical cutout portion 68 of rod 64 can be pushed back and forth to open or close passageway 58. See FIG. 4. Buttons 66 on either end of steel rod 64 can be color-coded to announce on/off state of outlet pathway 58. When RED button 66 is pushed into barrel syringe 38, the outlet is closed; when GREEN button 66 is pushed into barrel syringe 38, the outlet is open. The second safety feature is plastic, gas-permeable bushing 44 which fits snugly around plunger 46. Bushing 44 is designed to seat gas ampoule 10 onto the internal portion of needle assembly 42, and when ampoule 10 is seated and barrel-bushing locking caps 48 are in place, over both opposing arms 52 of bushing 44 and both opposing flanges 54 of syringe barrel 38, bushing 44 provides a positive rear stop for plunger 46 prohibiting plunger 46 from being withdrawn. See FIGS. 2 and 5. Two caps 48 are preferred, and preferably are made of metal. Caps 48 simply slide over flanges 54 on the syringe barrel 38 and flanges 52 on the plastic bushing 44, holding them together so that bushing 44 and plunger 46 cannot be removed from syringe barrel 38. Small holes in the face of bushing 44 next to plunger 46 are filled with granular adsorbent (i.e., activated charcoal) which serves as an additional safety feature. In case of internal breakage and release of radioactive gas, the charcoal will adsorb and prevent the release of the gas outside of syringe 14.

The use of a steel plunger 46 is preferred. The only purpose or use of plunger 46 is to push forward gas-tight teflon plunger tip 20 already in place in glass tube 16. There is no reason for plunger 14 to be gas-tight seated because plunger tip 20 is gas-tight.

To get an excellent fit between glass and teflon, use of a specially manufactured product such as "Trubore Tubing" made by the Ace Glass Co. is warranted or desired. Standard wall Pyrex is often too irregular, both from the standpoint of diameter and circularity. The "Trubore Tubing" is specially vacuum-formed glass around a precision-machined piece of metal of desired dimensions producing a piece of glass tubing with an internal diameter ±0.0004 inch throughout its entire length. More specifically, a piece of round metal is machined to specific dimension ±0.0004 inch. Melted glass, under vacuum and high heat, is poured around the machined piece of metal. This produces a piece of tubing with a consistent and controlled internal diameter throughout its length, but also gives a glass tube with a smooth internal surface, almost free from minor distortions that could scar or scratch a surface moving against it.

The use of activated charcoal between the inner tube 16 and outer barrel 28 is preferred. Thicker layers of absorbent 30 are preferred because the transmission of force in the vent of a shock would be absorbed to a certain extent by charcoal 30.

While, teflon is not impervious on a significant basis to penetration by all gases, e.g., methane or tritium, over an extended period of time, this does not provide any significant problem because invention device 10 is designed for quick usage without any significant period of storage. Also, while teflon may be altered in its mechanical properties by a strong radiation field, the entire idea of the invention gas ampoule is to do away with a strong radiation field by using only such small amounts of material as are needed for experimentation or procedure, i.e., the unit-dose concept.

By way of summary, the invention product is for shipment and delivery of radioactive gases. The gas ampoule, consisting of a glass tube with serum bottle stopper on one end and a plunger tip in the opposite end all fitting in a larger plastic tube threaded on each end with adsorbent between the tubes, is sealed onto the internal needle assembly via a bushing associated with the plunger and locked into the syringe barrel via barrel-bushing locking caps. The design of the invention product helps eliminate the possibility of personnel contamination due to an inadvertant exposure of contained radioactive gas.

The foregoing description of preferred embodiments of the invention has been presented for purposes of illustration and description. It is not intended to be exhaustive or to limit the invention to the precise form disclosed, and obviously many modifications and variation are possible in light of the above teachings. The embodiments were chosen and described in order to best explain the principles of the invention and its practical application to thereby enable one skilled in the art to best utilize the invention in various embodiments and with various modification as are suited to the particular use contemplated. It is intended that the scope of the invention be defined by the claims appended hereto.

What is claimed is:

1. A disposable gas ampoule holding or containing a gas such as a radioactive gas, comprising:
   (a) a cylindrical glass tube which is adapted to hold said gas;
   (b) a layer of absorbent material, which circumscribes and which contacts cylindrical glass tube (a) and which adsorbs said gas;
   (c) a plastic tube, which circumscribes and contacts absorbent material layer (b) and which is externally threaded on each of its end portions;
   (d) a cap, which is threaded onto a first end of plastic tube (c);
   (e) a cylindrical block, which is positioned in the first end of cylindrical glass tube (a) adjacent to cap (d), which contacts cylindrical glass tube (a), which is composed of a foamed material and which is impregnated with a gas adsorbent material;
   (f) a cylindrical plunger tip, which is located in the first end of cylindrical glass tube (a) in a gas-tight manner adjacent to cylindrical block (e);
   (g) an end stopper, which has a central cylindrical shaft that is positioned in the second end of cylindrical glass tube (a), the central cylindrical shaft contacting cylindrical glass tube (a), which has an outer rim that extends outward beyond the second end of cylindrical glass tube (a), and which has an outer lip that is affixed to the outer rim thereof, that contacts the outside of the second end of cylindrical glass tube (a) and that is positioned within plastic tube (c); and
   (h) a cap, which is threaded onto the second end of plastic tube (e).

2. The disposable gas ampoule as claimed in claim 1 wherein cylindrical glass tube (a) is precision-formed to give a consistent regularity in its internal diameter to within at least ±0.0004 inch throughout its entire length.

3. The disposable gas ampoule as claimed in claim 1 wherein absorbent material layer (b) is composed of activated charcoal.

4. The disposable gas ampoule as claimed in claim 1 wherein plastic tube (c) is composed of relatively shatter-proof plastic.

5. The disposable gas ampoule as claimed in claim 1 wherein caps (d) and (h) are composed of relatively shatter-proof plastic.

6. The disposable gas ampoule as claimed in claim claim 1 wherein cylindrical block (e) is composed of plastic.

7. The disposable gas ampoule as claimed in claim 6 wherein the gas absorbent material impregnated in cylindrical block (e) is composed of activated charcoal.

8. The disposable gas ampoule as claimed in claim 1 wherein plunger tip (f) is composed of teflon.

9. The disposable gas ampoule as claimed in claim 1 wherein end stopper (g) is composed of teflon.

10. A combination of the disposable gas ampoule as claimed in claim 1 and a syringe adapted to operably interface with said gas ampoule, said syringe having a cylindrical barrel, said disposable gas ampoule being positioned within said cylindrical barrel of said syringe, said caps (d) and (h) being removed from the ends of said gas ampoule, said cylindrical block (e) being removed from within said cylindrical glass tube (a), said syringe also having a bottom plate on one end of said barrel, a hollow syringe needle being positioned through the central axis of said bottom plate and being perpendicular to said bottom plate, one end of said needle thereby being external to said syringe barrel, the other end of said needle located within said syringe barrel having been forced through said end stopper (g) at its central axis, a mechanism for opening and closing said needle being positioned between said bottom plate of said syringe and said end stopper (g), said opening-and-closing mechanism being manually operable by at least one arm thereof which extends outward beyond said syringe barrel, said syringe further having a plastic bushing positioned in the other end of said cylindrical bushing, said plastic barrel having a longitudinal central bore, a plunger being positioned with its shaft slidably mounted in said longitudinal central bore of said plastic bushing and with its plunger end mounted in said cylindrical glass tube (a) in a slidable manner between gas-tight cylindrical plunger tip (f) and the first end of glass tube (a), said syringe barrel having a rim at the end located near said plastic bushing, said plastic bushing having a rim on its outer end which overlaps and contacts said rim of said syringe barrel, and a removable locking cap fitting over said rim of said syringe barrel and said rim of said plastic bushing.

11. The combination gas ampoule-syringe as claimed in claim 10 wherein said plastic bushing is composed of plastic.

12. The combination gas ampoule-syringe as claimed in claim 10 wherein said central bore of said plastic bushing contains holes filled with an absorbent.

13. The combination gas ampoule-syringe as claimed in claim 12 wherein said absorbent is activated charcoal.

14. The combination gas ampoule-syringe as claimed in claim 10 wherein said plastic bushing is composed of teflon.

15. The disposable gas ampoule as claimed in claim 1 wherein caps (d) and (h) are composed of metal.

16. The disposable gas ampoule as claimed in claim 1 wherein cylindrical block (e) is composed of teflon.

* * * * *